(12) United States Patent
Ogata et al.

(10) Patent No.: US 7,700,080 B2
(45) Date of Patent: Apr. 20, 2010

(54) METHOD OF SUPPRESSING MELANIN PRODUCTION BY METAL CHELATES OF LIPOYL AMINO ACID DERIVATIVES

(75) Inventors: Kazumi Ogata, Osaka (JP); Takahiro Sakaue, Hyogo (JP); Kazuhiko Ito, Hyogo (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 1138 days.

(21) Appl. No.: 10/472,726

(22) PCT Filed: Mar. 18, 2002

(86) PCT No.: PCT/JP02/02577

§ 371 (c)(1),
(2), (4) Date: Sep. 17, 2003

(87) PCT Pub. No.: WO02/076935

PCT Pub. Date: Oct. 3, 2002

(65) Prior Publication Data

US 2004/0092586 A1 May 13, 2004

(30) Foreign Application Priority Data

Mar. 19, 2001 (JP) .............................. 2001-078571

(51) Int. Cl.
*A61Q 19/02* (2006.01)
*A61K 8/02* (2006.01)

(52) U.S. Cl. ......................... 424/62; 424/401

(58) Field of Classification Search ........................ None
See application file for complete search history.

(56) References Cited

U.S. PATENT DOCUMENTS

| | | | |
|---|---|---|---|
| 3,238,224 A | | 3/1966 | Ohara et al. |
| 5,830,994 A | | 11/1998 | D'Hinterland et al. |
| 6,288,106 B1 | * | 9/2001 | Pearson et al. .............. 514/440 |
| 6,331,559 B1 | | 12/2001 | Bingham et al. |
| 6,337,315 B1 | * | 1/2002 | Mahe et al. .................... 514/2 |
| 2002/0107234 A1 | * | 8/2002 | Bingham et al. ............. 514/184 |

FOREIGN PATENT DOCUMENTS

| | | |
|---|---|---|
| JP | 60-11494 | 1/1985 |
| JP | 63-8316 | 1/1988 |
| JP | 2000-169371 | 6/2000 |
| WO | WO 00/20385 | 4/2000 |
| WO | WO 00/32235 | 6/2000 |
| WO | WO 01/49250 A2 | 7/2001 |

OTHER PUBLICATIONS

Sigel et al. Stability an structure of binary and ternary complexes of alpha-lipoate and lipoate derivatives with Mn2+, Cu2+ and Zn2+ in solution. Archives of Biochemistry and Biophysics. Apr. 15, 1978, vol. 187, issue 1, p. 208-214.*
Benedetto et al. 1982. Role of thiol compounds in mammalian melanin pigmentation. II. Glutathione and related enzymatic activities. The Journal of Investigative dermatology. 79:422-424.*
Daigo et al. Synthesis of some lipoayl amino acids and peptides. J. American Chemical Society. 1962, vol. 84, 663-665.*
"Untersuchungen zum Zusammenhang zwischen chemishcer Struktur und pharmakokinetischen Eigenschaflen von Tc-Thiolato-Komplexen", Johannsen et al., NUC-COMPACT- Apr. 1980, pp. 42-45. (Abstract/Translation Provided).
"Synthesis and characterization of iron derivatives of dihydrolipoic acid and dihydrolipoamide", Bonomi et al., Inorganica Chimica Acta, 195 (1992) 109-115.
"Untersuchungen zum Zusammenhang zwischen chemishcer Struktur und pharmakokinetischen Eigenschaflen von Tc-Thiolato-Komplexen", Johannsen et al., NUC-COMPACT- Apr. 1980, pp. 42-45.
"Lipoamidase is a multiple hydrolase", Oizumi et al., Biochem. J. (1990) 271, 45-49.
"Electrochemical Study on Dihydrolipoamide-Iron (II) Complex and Its Chemical Reactivity", Kijima et al., J. Org. Chem. 1985, 50, 2522-2524.
"Synthesis and characterization of metal derivatives of dihydrolipoic acid and dihydrolipoamide", Bonomi et al., Inorganica Chimica Acta, 192 (1992) 237-242.
Brown et al., "The Reactions of 1,3-Dimercaptopropane, Lipoic Acid, and Dihydrolipoic Acid with Metal Ions," J. Inorg. Nucl. Chem., 1970, vol. 32, pp. 2671-2675.

* cited by examiner

*Primary Examiner*—Lakshmi S Channavajjala
(74) *Attorney, Agent, or Firm*—Merchant & Gould P.C.

(57) ABSTRACT

A novel α-lipoic acid derivative represented by the following formula (I). It has a tyrosinase inhibiting activity, melanin production inhibitory activity, and elastase inhibiting activity. (I) (In the formula, M represents a metal and A denotes an amino acid residue bonded through the nitrogen atom.).

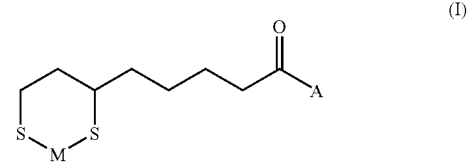

(I)

3 Claims, No Drawings

METHOD OF SUPPRESSING MELANIN PRODUCTION BY METAL CHELATES OF LIPOYL AMINO ACID DERIVATIVES

TECHNICAL FIELD

The present invention relates to novel α-lipoic acid derivatives, pharmacologically acceptable salts thereof and applications thereof.

BACKGROUND ART

Alfa-lipoic acid (also known as thioctic acid or 6,8-dithiooctanoic acid), a coenzyme occurring in mitochondria, has anti-oxidative activity and draws attention as a therapeutic agent for a variety of pathologic conditions induced by oxidative stress, such as arteriosclerosis and cataract. Its reduced state compound, dimercaptooctanoic acid, acts to restore reduced forms of glutathione or vitamin C back from their oxidized forms.

A class of α-lipoic acid derivatives, α-lipoylamino acids, in which α-lipoic acid is bound to glycine, methionine, glutamic acid, valine or the like, respectively are known (Japanese Patent Publication No. S42-1286, and its corresponding U.S. Pat. No. 3,238,224). Japanese Patent Application Publication No. 2000-169371 discloses a salt of α-lipoylaminoethylsulfonic acid with imidazole and its use as an enhancer of glutathione reductase activity.

Upon the above background, the present inventors succeeded in efficient synthesis of metal chelate compounds and their pharmacologically acceptable salts of reduced forms (dihydro-forms) of novel α-lipoylamino acids, found that these compounds possess a tyrosinase inhibiting activity, a melanin production suppressing activity and an elastase inhibiting activity, and completed the present invention through further studies.

DISCLOSURE OF INVENTION

Thus, the present invention relates to:

(1) an N-(6,8-dimercaptooctanoyl)amino acid metal chelate compound represented by the following formula (I),

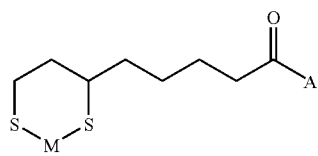

wherein M denotes a metal, and A denotes an amino acid which is bound via N, or a pharmacologically acceptable salt thereof (hereinafter referred to as the present compound), (2) the N-(6,8-dimercaptooctanoyl)amino acid metal chelate compound of the above-identified formula (I) or a pharmacologically acceptable salt thereof, wherein the N-(6,8-dimercaptooctanoyl)amino acid metal chelate compound is selected from the group consisting of N-(6,8-dimercaptooctanoyl)-α-amino acid metal chelates, N-(6,8-dimercaptooctanoyl)-β-amino acid metal chelates, N-(6,8-dimercaptooctanoyl)-γ-amino acid metal chelates, N-(6,8-dimercaptooctanoyl)-δ-amino acid metal chelates, and N-(6,8-dimercaptooctanoyl)-ε-amino acid metal chelates, (3) the N-(6,8-dimercaptooctanoyl)amino acid metal chelate compound of the above-identified formula (I) or a pharmacologically acceptable salt thereof, wherein the N-(6,8-dimercaptooctanoyl)amino acid metal chelate compound is selected from the group consisting of N-(6,8-dimercaptooctanoyl)-aminoethanesulfonic acid metal chelates, N-(6,8-dimercaptooctanoyl)glycine metal chelates, N-(6,8-dimercaptooctanoyl)aspartic acid metal chelates, N-(6,8-dimercaptooctanoyl)-6-aminohexanoic acid metal chelate, N-(6,8-dimercaptooctanoyl)-γ-amino-n-butyric acid metal chelates, N-(6,8-dimercaptooctanoyl)-phenylalanine metal chelates, N-(6,8-dimercaptooctanoyl)anthranilic acid metal chelates, N-(6,8-dimercaptooctanoyl) methionine metal chelates, and N-(6,8-dimercaptooctanoyl)cysteine metal chelates, (4) the N-(6,8-dimercaptooctanoyl)amino acid metal chelate compound of the above-identified formula (I) wherein the metal is zinc, or a pharmacologically acceptable salt thereof, (5) a medicament comprising the compound or a pharmacologically acceptable salts thereof defined in one of (1)-(4) above, (6) a tyrosinase inhibiting agent comprising the compound or a pharmacologically acceptable salt thereof defined in one of (1)-(4) above, (7) a melanin production suppressing agent comprising the compound or a pharmacologically acceptable salt thereof defined in one of (1)-(4) above, (8) a prophylactic or therapeutic agent for blotches and freckles or a suntan of the skin comprising the compound or a pharmacologically acceptable salt thereof defined in one of (1)-(4) above, (9) a whitening agent comprising the compound or a pharmacologically acceptable salt thereof defined in one of (1)-(4) above,

(10) a skin-beautifying agent comprising the compound or a pharmacologically acceptable salt thereof defined in one of (1)-(4) above,

(11) an elastase inhibiting agent comprising the compound or a pharmacologically acceptable salt thereof defined in one of (1)-(4) above,

(12) an anti-wrinkle agent comprising the compound or a pharmacologically acceptable salt thereof defined in one of (1)-(4) above,

(13) a cosmetic preparation comprising the compound or a pharmacologically acceptable salt thereof defined in one of (1)-(4) above,

(14) a method for inhibition of tyrosinase comprising administering to a human an effective amount of the compound or a pharmacologically acceptable salt thereof defined in one of (1)-(4) above,

(15) a method for suppression of melanin production comprising administering to a human an effective amount of the compound or a pharmacologically acceptable salt thereof defined in one of (1)-(4) above,

(16) a method for prophylaxis or therapeutic treatment of blotches and freckles or a suntan of the skin comprising administering to a human an effective amount of the compound or a pharmacologically acceptable salt thereof defined in one of (1)-(4) above,

(17) a method for whitening the skin comprising administering to a human an effective amount of the compound or a pharmacologically acceptable salt thereof defined in one of (1)-(4) above,

(18) a method for beautifying the skin comprising administering to a human an effective amount of the compound or a pharmacologically acceptable salt thereof defined in one of (1)-(4) above,

(19) a method for inhibiting elastase comprising administering to a human an effective amount of the compound or a pharmacologically acceptable salt thereof defined in one of (1)-(4) above,

(20) a method for prevention or therapeutic treatment of wrinkles comprising administering to a human an effective amount of the compound or a pharmacologically acceptable salt thereof defined in one of (1)-(4) above,

(21) use of the compound or a pharmacologically acceptable salt thereof defined in one of (1)-(4) above for the manufacture of a medicament,

(22) use of the compound or a pharmacologically acceptable salt thereof defined in one of (1)-(4) above for the manufacture of a tyrosinase inhibiting agent,

(23) use of the compound or a pharmacologically acceptable salt thereof defined in one of (1)-(4) above for the manufacture of a melanin production suppressing agent,

(24) use of the compound or a pharmacologically acceptable salt thereof defined in one of (1)-(4) above for the manufacture of a prophylactic or therapeutic agent for blotches and freckles or a suntan of the skin,

(25) use of the compound or a pharmacologically acceptable salt thereof defined in one of (1)-(4) above for the manufacture of a whitening agent,

(26) use of the compound or a pharmacologically acceptable salt thereof defined in one of (1)-(4) above for the manufacture of a skin-beautifying agent,

(27) use of the compound or a pharmacologically acceptable salt thereof defined in one of (1)-(4) above for the manufacture of a elastase inhibiting agent,

(28) use of the compound or a pharmacologically acceptable salt thereof defined in one of (1)-(4) above for the manufacture of an anti-wrinkle agent, and

(29) use of the compound or a pharmacologically acceptable salt thereof defined in one of (1)-(4) above for the manufacture of a cosmetic preparation.

The present compound is of a structure consisting of α-lipoic acid that is amide-bonded with an amino acid and a chelated metal therewith, and is a novel compound that has not been found in a literature. In the present invention, amino acid means α-amino acid, β-amino acid, γ-amino acid, δ-amino acid and ε-amino acid, which have in their molecule a carboxyl group together with an amino group, and aminomethylcyclohexanoic acid and anthranilic acid, as well as aminoethanesulfonic acid (taurine), which has in the molecule a sulfonic acid group together with an amino group. Examples of α-amino acids include glycine, alanine, valine, leucine, isoleucine, serine, threonine, tyrosine, cysteine, methionine, aspartic acid, asparagine, glutamic acid, glutamine, arginine, lysine, histidine, phenylalanine, tryptophan, etc. Examples of β-amino acids include β-alanine. Examples of γ-amino acids include γ-amino-n-butyric acid (GABA) and carnitine. Examples of δ-amino acids include 5-aminolevulinic acid, and 5-aminovaleric acid. Examples of ε-amino acids include 6-aminohexanoic acid. Among those amino acids, anthranilic acid, aminoethanesulfonic acid, methionine, phenylalanine, γ-amino-n-butyric acid and 6-aminohexanoic acid are preferred.

As a metal in the metal chelate compounds of the present invention, preferably employed are zinc and cobalt, which are divalent metals, iron, which is a divalent or trivalent metal, and tetravalent germanium. Among them, zinc, which is a divalent metal, is particularly preferred. The present compound is an easily purified, stable compound.

Examples of pharmacologically acceptable salts of the present compound include alkali metal salts such as sodium salt and potassium salt and alkali earth metal salts such as calcium salt and magnesium salt. Any other salts may be employed as desired for the purpose of the present invention insofar as they are pharmacologically acceptable.

Further, monohydrates, dihydrates, 1/2 hydrates, 1/3 hydrates, 1/4 hydrates, 2/3 hydrates, 3/2 hydrates and 6/5 hydrates are also included in the present invention.

In general, for the synthesis of α-lipoylamino acids, intermediate compounds, an amino acid is esterified on its carboxyl group to get the group protected, then converted to an acid amide with α-lipoic acid using a dehydration condensation agent, and finally subjected to saponification. However, synthesis is difficult by this method where aminoethanesulfonic acid is employed.

The present compound may be synthesized as desired by, or according to, e.g., the following scheme of synthesis.

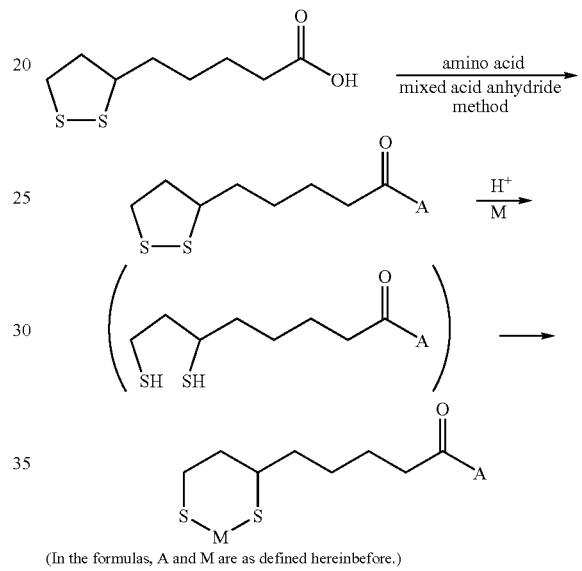

(In the formulas, A and M are as defined hereinbefore.)

As a result of a study for an efficient production of α-lipoylamino acid, an intermediate for the present compound, it was found that the aimed α-lipoylamino acid is obtained in high yield when synthesized by the mixed acid anhydride method (MA). Briefly, α-lipoic acid dissolved in an organic solvent (e.g., chloroform, tetrahydrofuran, acetonitrile, etc.) is reacted with a mixed acid anhydride reagent such as a halogenated carbonic acid ester (such as ethyl carbonyl chloride, butyl carbonyl chloride), isobutyloxycarbonyl chloride, diethylacetyl chloride, trimethylacetyl chloride and the like to form an mixed acid anhydride of α-lipoic acid at −15 to −5° C. in the presence of tertiary amine (such as triethylamine, tributylamine, N-methylmorpholine (NMM)). The length of time of the reaction is from 1-2 minutes to several tens of minutes. Then, an amino acid dissolved in alcohol, water or a mixture solution thereof in the presence of a base (such as sodium hydroxide, potassium hydroxide, or a tertiary amine such as triethylamine or tributylamine) is added and reacted. Subsequent recrystallization from a suitable solvent, e.g., water or alcohol, gives α-lipoylamino acid in high yield.

Reduction of thus obtained α-lipoylamino acid with a metal and an acid gives, via a dihydro compound, a chelate compound of the present invention in high yield. Examples of acids employed in the reduction of a stable α-lipoylamino acid includes inorganic acids such as hydrochloric acid and sulfuric acid and organic acids such as acetic acid and citric acid. In the case of a zinc chelate compound, the two —SH groups (mercapto group) in its molecule are thought to bind with one zinc atom.

Melanin in the skin is produced by melanocytes. Tyrosinase has long been known as a sole rate-controlling enzyme which regulates melanin production. Tyrosinase is catalyzed by three enzymes, i.e., tyrosine hydroxylase, 3,4-dihydroxyphenylalanine (DOPA) oxidase and 5,6-dihydroxyindole (DHI) oxidase, which play important roles in early as well as late reactions in melanin production. As evident from the test examples mentioned below, the present compound suppresses melanin production by inhibiting tyrosinase, the rate-controlling enzyme, via inhibition of tyrosine hydroxylase.

On the other hand, elastase is an enzyme which splits elastin, an elastic structure protein having a number of cross links among its peptide chains and occurring in tissues with considerable extensibility such as the skin. Therefore, inhibition of elastase in the skin would be useful for prevention of wrinkles and maintenance of the beauty of the skin, for it would serve to maintain the extensibility and elasticity of the skin. As evident from the test examples described below, the present compound also has an elastase inhibiting activity.

Thus, the present compound has, as its features, melanin production suppressing activity and elastase inhibiting activity.

Therefore, the present compound is useful as a prophylactic or therapeutic agent for blotches and freckles or suntan of the skin, a whitening agent, a skin-beautifying agent and an anti-wrinkle agent.

The present compound also exhibits anti-oxidation activity and radical-suppressing activity (eliminating a stable radical, 1,1-diphenyl-2-picrylhydroradical (DPPH)). That the present compound has such activity is demonstrated by the fact that one mole of the present compound is required to reduce and decolorize one mole of iodine ($I_2$), which is consistent with what is theoretically calculated, and the present compound itself is thereby oxidized back to α-lipoylamino acid (see the following scheme).

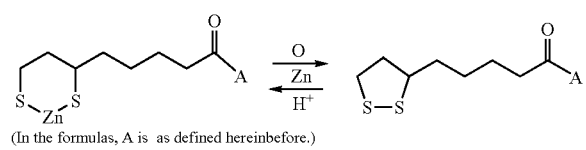

(In the formulas, A is as defined hereinbefore.)

The present compound is useful for prophylaxis and treatment of a variety of disorders caused by oxidative stress in mammals (e.g., bovine, horse, rabbit, mouse, rat, human), e.g., ischemic cardiovascular disease, cerebral ischemia, arteriosclerosis, diabetes mellitus and cataract.

When the present compound is used as a medical drug, one of the species of the present compound, or two or more of them in combination, may be employed as desired according to purpose and need.

The present compound is used as desired orally or parenterally as a drug for the treatment of the aforementioned disorders. As for preparation forms, it may be provided in any form by a known method, e.g., solid preparations such as tablets, granules, powder, capsules, or liquid preparations such as injection or eye drops. These preparations may contain conventional additives as desired, such as diluents, binders, thickening agents, dispersing agents, reabsorption enhancers, buffers, surfactants, solubilizing agents, preservatives, emulsifiers, isotonizers, stabilizers, pH adjusting agents, etc.

The doses of the present compound, when used as a medical drug, will vary according to the employed species of the present compound, the body weight and age of a given patient, the disorder to be treated and its condition and the way of administration. When used for ischemic cardiovascular diseases, cerebral ischemia, arteriosclerosis or diabetes mellitus, the doses for an adult are about 1 mg to about 30 mg per day given at a time in the case of an injection and about 1 mg to about 100 mg at a time, administered several times a day, in the case of an oral preparation. When used as an anti-cataract drug, eye drops containing about 0.01 to 5 (w/v) % are preferably applied several times a day, several drops at each time.

A medical drug containing the present compound may also contain other ingredients having the same or different pharmacological activity insofar as they do not act counter to the purpose of the present invention.

The compound of the present invention may be added as desired to creams, facial masking agents, powders, lotions, toilet waters for prophylaxis or treatment of blotches and freckles or suntan of the skin, or for whitening, skin beatifying or anti-wrinkle activity. When the present compound is added to cosmetic products, other additives conventionally used in cosmetic products may also be employed, such as diluents, stabilizers, pigments, fragrant materials, ultraviolet absorbents, antioxidants, preservatives, metal chelating agents and organic acids.

When the present compound is used for cosmetic products, it is added usually at about 0.001 to 5 (w/w) %, preferably at about 0.005 to 2 (w/w) %, although this depends on the employed species of the compound, the type of the cosmetic product and the purpose of the addition.

EXAMPLES

The present invention will be described below in further detail with reference to the reference examples, examples and test examples. However, the scope of the present invention is not limited by them.

Reference Example 1

N-α-lipoylaminoethanesulfonic acid sodium salt

To 6.2 g of DL-α-lipoic acid, dissolved in 60 ml of chloroform, was added 3.2 g of triethylamine, and cooled at −5° C. To this, 3.3 g of ethyl carbonyl chloride was slowly added dropwise and, 15 minutes after the completion of the addition, 4.5 g of aminoethanesulfonic acid and 1.5 g of sodium hydroxide dissolved in 60 ml of methanol were added at once, and stirred for 15 minutes at the same temperature and further one hour at room temperature. To this was added a solution of 1.5 g of sodium hydroxide dissolved in 50 ml of methanol, the solvent was condensed under reduced pressure to ⅓ of the initial volume, 60 ml of ethanol was added, and precipitated crystals were collected by filtration. Recrystallized of this from water-methanol gave 5.8 g of white crystals of aimed sodium salt. Melting point: 235-237° C. TLC, Rf=0.53 (n-butanol:acetic acid:water=4:1:2)

Elemental Analysis: For $C_{10}H_{17}NO_4S_3Na \cdot H_2O$.

Calculated: C, 34.08; H, 5.43; N, 3.97.

Found: C, 34.23; H, 5.54; N, 3.80.

Reference Example 2

N-α-lipoylaminoethanesulfonic acid potassium salt

The same procedure as Reference Example 1 was followed except that sodium hydroxide in Reference Example 1 was replaced with 4.0 g of potassium hydroxide. Recrystallization from water/methanol gave 6.5 g of white crystals of aimed potassium salt. Melting point: 240-242° C.

Reference Example 3

N-α-lipoylaminoethanesulfonic acid calcium and magnesium salts

The sodium salt obtained in Reference Example 1 was dissolved in water, desalted with a sulfonic acid type resin into a free acid form, and neutralized with calcium carbonate or basic magnesium carbonate to give soluble calcium and magnesium salts, respectively. Melting point: over 300° C., respectively.

Reference Example 4

N-α-lipoyl-6-aminohexanoic acid sodium salt

Using 4.2 g of DL-α-lipoic acid and 3.0 g of 6-aminohexanoic acid, the reaction was conducted in the same manner as Reference Example 1. Recrystallization from ethanol gave 3.0 g of yellowish white crystals of the aimed compound. Melting point: 200-202° C. (decomp.). TLC, Rf=0.84 (chloroform:methanol:water=5:4:1)

Reference Example 5

N-α-lipoylaspartic acid disodium salt

Using 4.2 g of DL-α-lipoic acid and 2.9 g of L-aspartic acid, the reaction was conducted in the same manner as Reference Example 1. Recrystallization from water/methanol gave 4.5 g of white crystals of the aimed compound. Melting point: over 300° C. TLC, Rf=0.47 (chloroform:methanol:water=4:1:2)

Reference Example 6

N-α-lipoyl-γ-amino-n-butyric acid sodium salt

Using 4.2 g of DL-α-lipoic acid and 2.3 g of γ-amino-n-butyric acid, the reaction was conducted in the same manner as Reference Example 1. Recrystallization from ethanol gave 4.0 g of sodium salt, the aimed compound. Melting point: gradual decomposition starting at about 235° C. TLC, Rf=0.76 (chloroform:methanol:water=4:1:2)

Reference Example 7

N-α-lipoylglycine sodium salt

Using 4.2 g of DL-α-lipoic acid and 1.9 g of glycine, the reaction was conducted in the same manner as Reference Example 1. Recrystallization from methanol/ethanol gave 4.5 g of pale yellow crystals of the aimed compound. Melting point: 218-220° C. (decomp.) TLC, Rf=0.64 (chloroform:methanol:water=4:1:2)

Reference Example 8

N-α-lipoylphenylalanine

Using 4.2 g of DL-α-lipoic acid and 3.5 g of phenylalanine, the reaction was conducted in the same manner as Reference Example 1. After evaporation of the solvent and acidification with hydrochloric acid, extraction was carried out with ethyl acetate. Following washing with water, ethyl acetate was evaporated. The crystalline residue was recrystallized from ethanol/isopropyl ether, giving 5.4 g of pale yellow crystals. Melting point: 154-156° C. TLC, Rf=0.86 (nbutanol:acetic acid:water=4:1:2)

Reference Example 9

N-α-lipoylanthranilic Acid Sodium Salt

Using 4.2 g of DL-α-lipoic acid and 2.9 g of anthranilic acid, the same procedure followed as Reference Example 1 gave 3.6 g of white crystals. Melting point: over 300° C. TLC, Rf=0.89 (n-butanol:acetic acid:water=4:1:2)

Reference Example 10

N-α-lipoylmethionine

Using 4.2 g of DL-α-lipoic acid and 3.5 g of L-methionine, the same procedure followed as Reference Example 8 gave 4.0 g of pale yellow crystals. Melting point: 108-109° C. TLC, Rf=0.81 (n-butanol:acetic acid:water=4:1:2)

Reference Example 11

N-α-lipoylcysteine sodium salt 4.2 g of DL-α-lipoic acid and 2.2 g of triethylamine were dissolved in 60 ml of tetrahydrofuran and cooled at −5° C. To this, 2.3 g of ethyl carbonyl chloride was slowly added dropwise and, 6 minutes after the completion of the addition, a solution of 2.6 g of L-cysteine and 2.5 g of triethylamine dissolved in 20 ml of water was added and reacted as in Reference Example 1. After acidification with hydrochloric acid, extraction was carried out with ethyl acetate. Following washing, ethyl acetate was evaporated, and the residue was dissolved in ethanol. By gradual addition of sodium hydroxide in methanol to adjust the pH to 7, 4.3 g of precipitated white crystals were obtained. Melting point: gradual decomposition starting at about 150° C. TLC, Rf=0.72 (n-butanol:acetic acid:water=4:1:2). For a product where N-ethylmaleimide was added, Rf=0.69 was found.

Reference Example 12

N-α-lipoyl-5-hydroxytryptophan

Using 4.2 g of DL-α-lipoic acid and 5.0 g of L-5-hydroxytryptophan, the same procedure followed as Reference Example 8 gave 6.4 g of white crystals. Melting point: 118-120° C. TLC, Rf=0.85 (n-butanol:acetic acid:water=4:1:2)

Example 1

N-(6,8-dimercaptooctanoyl)aminoethanesulfonic acid sodium salt zinc chelate compound 5.0 g of the compound in the form of sodium salt obtained in Reference Example 1 was dissolved in 100 ml of water, and to this were added 10 ml of acetic acid and 1.3 g of zinc powder. After one-hour stirring at 50° C., unreacted zinc was filtered off, the filtrate concentrated under reduced pressure, and ethanol was added. Precipitated white crystals were collected by filtration, dissolved in water, adjusted of the pH to about 8 with sodium bicarbonate, and concentrated. Methanol then was added and precipitated white crystals were collected by filtration. Recrystallization from water/methanol gave 4.3 g of the aimed compound. Melting point: decomposition starting at about 293° C. TLC, Rf=0.51 (n-butanol:acetic acid:water=:4:1:2)

| Elemental Analysis: For $C_{10}H_{17}NO_4S_3NaZn.H_2O$ | | | |
|---|---|---|---|
| Calculated: | C, 28.75 | H, 4.58 | N, 3.35 |
| Found: | C, 28.56 | H, 4.69 | N, 3.13 |

Example 2

N-(6,8-dimercaptooctanoyl)aminoethanesulfonic acid potassium salt zinc chelate compound The same procedure as in Example 1 was followed using 6.5 g of the compound obtained in Reference Example 2, giving 5.0 g of the aimed compound.

| Elemental Analysis: For $C_{10}H_{17}NO_4S_3KZn.1/2H_2O$ | | | |
|---|---|---|---|
| Calculated: | C, 28.27 | H, 4.27 | N, 3.30 |
| Found: | C, 28.38 | H, 4.52 | N, 3.10 |

Example 3

N-(6,8-dimercaptooctanoyl)glycine sodium salt zinc chelate compound

The same procedure as in Example 1 was followed using 4.5 g of the compound obtained in Reference Example 7, giving 3.9 g of the aimed compound. Melting point: decomposition starting at about 297° C. TLC, Rf=0.64 (chloroform:methanol:water=4:1:2)

| Elemental Analysis: For $C_{10}H_{16}NO_3S_2NaZn.H_2O$ | | | |
|---|---|---|---|
| Calculated: | C, 32.57 | H, 4.92 | N, 3.80 |
| Found: | C, 32.43 | H, 4.83 | N, 3.74 |

Example 4

N-(6,8-dimercaptooctanoyl)aspartic acid sodium salt zinc chelate compound

Reduction was performed as in Example 1 using 3.0 g of the compound obtained in Reference Example 5. Precipitated white crystals were collected by filtration and suspended in water, dissolved at pH 7-8 with sodium hydroxide, insoluble matter was filtered off, and filtrate concentrated. Methanol was added and precipitated white crystals were collected by filtration, giving 2.3 g of the aimed compound. Melting point: decomposition starting at about 295° C. TLC, Rf=0.53 (chloroform:methanol:water=5:4:1)

| Elemental Analysis: For $C_{12}H_{17}NO_5S_2NaZn.H_2O$ | | | |
|---|---|---|---|
| Calculated: | C, 32.11 | H, 4.29 | N, 3.12 |
| Found: | C, 32.09 | H, 4.44 | N, 3.10 |

Example 5

N-(6,8-dimercaptooctanoyl)-6-aminohexanoic acid sodium salt zinc chelate compound 3.0 g of the compound obtained in Reference Example 4 was dissolved in 70 ml of 50% tetrahydrofuran and reduced as in Example 1. The solvent was evaporated and precipitated white crystals were collected by filtration. Melting point: 215-217° C. These were suspended in water, and dissolved at pH 7-8 with sodium hydroxide. The solution was concentrated and methanol was added. Precipitated white crystals were collected by filtration, giving 2.0 g of the aimed compound. Melting point: decomposition starting at about 295° C. TLC, Rf=0.84 (chloroform:methanol:water=5:4:1)

| Elemental Analysis: For $C_{14}H_{24}NO_3S_2NaZn.H_2O$ | | | |
|---|---|---|---|
| Calculated: | C, 39.58 | H, 6.17 | N, 3.30 |
| Found: | C, 39.38 | H, 6.02 | N, 3.13 |

Example 6

N-(6,8-dimercaptooctanoyl)-γ-amino-n-butyric acid sodium salt zinc chelate compound 4.0 g of the compound obtained in Reference Example 6 was reduced and worked out as in Example 1, giving 2.1 g of white crystals of the aimed compound. Melting point: decomposition starting at about 297° C. TLC, Rf=0.70 (chloroform:methanol:water=5:4:1)

| Elemental Analysis: For $C_{12}H_{20}NO_3S_2NaZn.H_2O$ | | | |
|---|---|---|---|
| Calculated: | C, 36.32 | H, 5.59 | N, 3.53 |
| Found: | C, 36.08 | H, 5.81 | N, 3.29 |

Example 7

N-(6,8-dimercaptooctanoyl)phenylalanine sodium salt zinc chelate compound

To 5.4 g of the compound obtained in Reference Example 8 were added 80 ml of 30% methanol, 2.0 g of zinc powder, 10 ml of acetic acid and 20 ml of 2 N HCl. After 3-hour stirring at 50° C., unreacted zinc was filtered off, and the filtrate was concentrated. Following addition of water, precipitated oily matter was collected. For conversion to a sodium salt, this was dissolved in methanol and pH adjusted to 7 with sodium hydroxide/methanol. Precipitated crystals were collected by filtration, giving 3.9 g. Melting point: gradual decomposition starting at about 270° C. TLC, Rf=0.82 (n-butanol:acetic acid:water=4:1:2)

| Elemental Analysis: For $C_{17}H_{23}NO_3S_2NaZn.1/2H_2O$ | | | |
|---|---|---|---|
| Calculated: | C, 45.39 | H, 5.15 | N, 3.11 |
| Found: | C, 45.55 | H, 5.33 | N, 3.23 |

Example 8

N-(6,8-dimercaptooctanoyl)anthranilic acid sodium salt zinc chelate compound

The same procedure as Example 7 was followed using 3.6 g of the compound obtained in Reference Example 9, giving 2.1 g of white crystals. Melting point: decomposition starting at about 290° C. TLC, Rf=0.88 (nbutanol:acetic acid:water=4:1:2)

| Elemental Analysis: For $C_{15}H_{18}NO_3S_2NaZn.H_2O$ | | | |
|---|---|---|---|
| Calculated: | C, 41.81 | H, 4.68 | N, 3.25 |
| Found: | C, 41.98 | H, 4.64 | N, 3.26 |

Example 9

N-(6,8-dimercaptooctanoyl)methionine zinc chelate compound

The same procedure was followed as Example 7 using 4.0 g of the compound obtained in Reference Example 10, giving 2.8 g of the aimed compound, free acid. Melting point: gradual decomposition starting at about 260° C. TLC, Rf=0.82 (n-butanol:acetic acid:water=4:1:2)

| Elemental Analysis: For $C_{13}H_{23}NO_3S_3Zn.1.5H_2O$ | | | |
|---|---|---|---|
| Calculated: | C, 36.32 | H, 6.10 | N, 3.26 |
| Found: | C, 36.17 | H, 5.78 | N, 3.34 |

Example 10

N-(6,8-dimercaptooctanoyl)cysteine zinc chelate compound

To 5.7 g of the compound obtained in Reference Example 11 were added 100 ml of 50% methanol, 3.5 g of zinc powder, 10 ml of acetic acid and 40 ml of 2 N hydrochloric acid. After 3-hour stirring at 50° C., unreacted zinc was filtered off, the filtrate concentrated to about ½. The pH of this was adjusted to 3-4 with 2 N sodium hydroxide and precipitated white crystals were collected by filtration and washed with 3% acetic acid and water. They were dissolved in 1% sodium hydroxide, acidified with acetic acid, and precipitated crystals was collected by filtration, washed with water and methanol, and dried. Melting point: decomposition starting at about 280° C. TLC (after dissolving by neutralization with ammonium water), Rf=0.71 (chloroform:methanol:water=5:4:1)

| Elemental Analysis: For $C_{22}H_{36}N_2O_6S_6Zn.3H_2O$ | | | |
|---|---|---|---|
| Calculated: | C, 31.79 | H, 4.61 | N, 3.37 |
| Found: | C, 31.98 | H, 4.77 | N, 3.14 |

Test Example 1

Tyrosine Hydroxylase Inhibiting Activity of the Present Compound

The present compound was examined for tyrosine hydroxylase inhibiting activity.

(Test Method)

Tyrosine hydroxylase from rat brain was used in the test.

A test compound added to 100 μM tyrosine containing L-[3,5-$^3$H] tyrosine (0.5 μCi/assay), 1 mg of tyrosine hydroxylase, 0.2 mM of (6R)-5,6,7,8-tetrahydro-L-biopterin, 1.8 mg/ml catalase, 5 mM dithiothreitol (in MES buffer, pH 6.0) was incubated at 37° C. for 40 minutes. The reaction was terminated by addition of 7.5% charcoal in 1 M hydrochloric acid.

$^3$H$_2$O derived from 3,4-dihydroxyphenylalanine (DOPA) was determined by liquid scintillation.

(Test Compound)

The compounds of Reference Example 1, Example 1, and α-lipoic acid (final concentration: 0.1 mM, 1 mM).

(Test Results)

The results are shown in Table 1.

TABLE 1

| Tyrosine Hydroxylase Inhibiting Activity of The Present Compound | | |
|---|---|---|
| Concentration (%) | 0.1 mM | 1 mM |
| Compound of Reference Example 1 | 11 | 10 |
| Compound of Example 1 | 15 | 53 |
| α-lipoic acid | 2 | 1 |

Values are inhibition rates (%)

As evident from Table 1, tyrosine hydroxylase inhibiting activity was noted with the present compound. In contrast, α-lipoic acid exhibited no tyrosine hydroxylase inhibiting activity. Thus, the present compound was found to inhibit tyrosinase, an enzyme regulating melanin production.

Test Example 2

Melanin Production Suppressing Activity of the Present Compound (Test Method)

B16-F0 melanoma cell line of mouse origin, purchased from Dainippon Pharmaceutical Co., Ltd. was used in the experiment. In 60-mm petri dish, 200,000 cells were incubated for five days in a medium (D-MEM*+10% FBS*) supplemented with 0.1% D-glucosamine hydrochloride, an inhibitor of carbohydrate synthesis, to halt melanin synthesis and turn the culture white. Following the 5-day culture, the cells were washed with PBS(−)* to remove D-glucosamine hydrochloride, and 2 mM theophylline (250-fold concentrated solution/distilled water), a phosphodiesterase inhibitor, was added to raise intracellular cAMP and thereby promote the recovery of tyrosinase synthesis. At the same time, a test compound (250-fold concentrated solution/PBS(−)) was added. Three days after the addition of theophylline and the test compound, the cells were harvested by trypsin treatment. The cell pellets were resuspended in 1 ml of PBS(−), 0.1 ml of which was used for counting cells, and 0.9 ml for melanin determination. Determination of melanin was carried out by washing the cell pellets once with 5% trichloroacetic acid, ethanol/diethyl ether (3:1), and then diethyl ether, adding 1 ml of 2 N NaOH to lyse the cells, measuring optical density at 420 nm, and comparing the result with a calibration curve produced with reference standard.

*(NB)

D-MEW: Dulbecco's Modified EAGLE MEDIUM "Nissui" (2)

FBS: Fetal Bovine Serum Certified, Origin: United States

PBS(−): Dulbecco's PBS(−) "Nissui"

The results are shown in Table 2.

TABLE 2

Melanin Production Suppressing Activity of The Present Compound

|  | Melanin amount (% of control) |
|---|---|
| Control | 100.00 |
| Kojic acid 0.1 mM | 92.70 |
| Kojic acid 0.3 mM | 88.04 |
| Kojic acid 1 mM | 68.80 |
| Kojic acid 10 mM | 18.73 |
| Arbutin 0.1 mM | 97.29 |
| Arbutin 0.3 mM | 88.86 |
| Arbutin 1 mM | 83.02 |
| N-(6,8-dimercaptooctanoyl)aminoethanesulfonic acid Na—Zn 0.03 mM | 78.33 |
| N-(6,8-dimercaptooctanoyl)aminoethanesulfonic acid Na—Zn 0.1 mM | 30.01 |
| N-(6,8-dimercaptooctanoyl)aminoethanesulfonic acid Na—Zn 0.3 mM | 12.28 |
| N-(6,8-dimercaptooctanoyl)-6-aminohexanoic acid Na—Zn 0.03 mM | 64.43 |
| N-(6,8-dimercaptooctanoyl)-6-aminohexanoic acid Na—Zn 0.1 mM | 27.69 |
| N-(6,8-dimercaptooctanoyl)-6-aminohexanoic acid Na—Zn 0.3 mM | 9.85 |
| N-(6,8-dimercaptooctanoyl)-γ-amino-n-butyric acid Na—Zn 0.03 mM | 61.18 |
| N-(6,8-dimercaptooctanoyl)-γ-amino-n-butyric acid Na—Zn 0.1 mM | 29.20 |
| N-(6,8-dimercaptooctanoyl)-γ-amino-n-butyric acid Na—Zn 0.3 mM | 9.73 |
| N-(6,8-dimercaptooctanoyl)methionine Zn 0.03 mM | 63.05 |
| N-(6,8-dimercaptooctanoyl)methionine Zn 0.1 mM | 50.18 |
| N-(6,8-dimercaptooctanoyl)methionine Zn 0.3 mM | 16.41 |
| N-(6,8-dimercaptooctanoyl)phenylalanine Na—Zn 0.03 mM | 71.43 |
| N-(6,8-dimercaptooctanoyl)phenylalanine Na—Zn 0.1 mM | 37.78 |
| N-(6,8-dimercaptooctanoyl)anthranilic acid Na—Zn 0.03 mM | 72.47 |
| N-(6,8-dimercaptooctanoyl)anthranilic acid Na—Zn 0.1 mM | 47.64 |
| N-(6,8-dimercaptooctanoyl)anthranilic acid Na—Zn 0.3 mM | 16.74 |

In the table, Zn denotes zinc chelate, and Na—Zn zinc chelate of sodium salt (the same applies below).

As evident from Table 2, N-(6,8-dimercaptooctanoyl)aminoethanesulfonic acid Na—Zn, N-(6,8-dimercaptooctanoyl)aminohexanoic acid Na—Zn, N-(6,8-dimercaptooctanoyl)-γ-amino-n-butyric acid Na—Zn, N-(6,8-dimercaptooctanoyl)methionine Zn, N-(6,8-dimercaptooctanoyl)phenylalanine Na—Zn, and N-(6,8-dimercaptooctanoyl)anthranilic acid Na—Zn exhibited potent suppressive action on melanin production, which was significantly more potent than arbutin or kojic acid, compounds so far used as whitening agent.

Test Example 3

Elastase Inhibiting Activity of the Present Compound

Test Method 96-well plates were used. 1 mM of Suc(Ome)-Ala-Ala-Pro-Val-MCA, 30 μl of a test sample, 210 μl of Tris-NaCl Buffer (25° C., pH 7.5) and 30 μl of 1 unit/ml elastase were added and fluorescence was measured every minute (Ex. 360/40 nm, Em. 460/40 nm). Inhibition rates of elastase activity were determined based on a calibration curve produced with AMC (7-amino-4-methyl-coumarin) reference standard.

The results are shown in Table 3.

TABLE 3

Esterase Inhibiting Activity of The Present Compound

|  | Elastase inhibition rate (%) |
|---|---|
| Elastinal 0.03 mM | 25.29 |
| Elastinal 0.1 mM | 56.87 |
| Elastinal 0.3 mM | 77.45 |
| Elastinal 1 mM | 93.01 |
| α-lipoic acid 0.03 mM | −2.94 |
| α-lipoic acid 0.1 mM | 11.76 |
| α-lipoic acid 0.3 mM | 10.29 |
| N-(6,8-dimercaptooctanoyl)-6-aminohexanoic acid Na—Zn 0.03 mM | 94.74 |
| N-(6,8-dimercaptooctanoyl)-γ-amino-n-butyric acid Na—Zn 0.03 mM | 78.95 |
| N-(6,8-dimercaptooctanoyl)methionine Zn 0.03 mM | 7.41 |
| N-(6,8-dimercaptooctanoyl)methionine Zn 0.1 mM | 68.52 |
| N-(6,8-dimercaptooctanoyl)methionine Zn 0.3 mM | 88.89 |
| N-(6,8-dimercaptooctanoyl)phenylalanine Na—Zn 0.03 mM | 83.33 |
| N-(6,8-dimercaptooctanoyl)anthranilic acid Na—Zn 0.03 mM | 24.07 |
| N-(6,8-dimercaptooctanoyl)anthranilic acid Na—Zn 0.1 mM | 48.15 |
| N-(6,8-dimercaptooctanoyl)anthranilic acid Na—Zn 0.3 mM | 72.22 |

As evident from Table 3, elastase inhibiting activity comparable to Elastinal was noted with N-α-(6,8-dimercaptooctanoyl)-6-aminohexanoic acid Na—Zn, N-α-(6,8-dimercaptooctanoyl)-γ-amino-n-butyric acid Na—Zn, N-α-(6,8-dimercaptooctanoyl)methionine Zn, N-α-(6,8-dimercaptooctanoyl)phenylalanine Na—Zn, N-α-(6,8-dimercaptooctanoyl)anthranilic acid Na—Zn. On the other hand, α-lipoic acid did not show any elastase inhibiting activity.

From the results, the present compound was found to be useful as an anti-wrinkle agent.

Preparation Example 1

Injection

| | | |
|---|---|---|
| The compound of Example 1 | | 2.0 mg |
| D-mannitol | | 5.0 g |
| Distilled water for injection | Total amount | 100 ml |

Using the above ingredients, an injection is prepared by a conventional method.

Preparation Example 2

Eye Drops

| | | |
|---|---|---|
| The compound of Example 2 | | 0.5 g |
| Sodium chloride | | 0.5 g |
| Boric acid | | 0.7 g |
| Borax | | 0.3 g |
| Methyl p-hydroxybenzoate | | 0.026 g |
| Propyl p-hydroxybenzoate | | 0.014 g |
| Sterile purified water | Total amount | 100 ml |

Using the above ingredients, eye drops are prepared by a conventional method.

Preparation Example 3

Tablets

| | |
|---|---|
| The compound of Example 1 | 50 mg |
| Lactose | 80 mg |
| Potato starch | 17 mg |
| Polyethylene glycol | 3 mg |

Using the above ingredients as the materials for one tablet, tables are prepared by a conventional method.

Preparation Example 4

Cosmetic Cream

| | |
|---|---|
| The compound of Example 7, 8 or 9 | 0.5 g |
| Stearic acid | 2.0 g |
| Stearyl alcohol | 7.0 g |

-continued

| | |
|---|---|
| Squalane | 5.0 g |
| Octyldecanol | 6.0 g |
| Polyoxyethylene cetyl ether | 3.0 g |
| Glycerol monostearate | 2.0 g |
| Propylene glycol | 5.0 g |
| Methyl p-hydroxybenzoate | 0.2 g |
| Propyl p-hydroxybenzoate | 0.1 g |
| Sterile purified water | 73.7 g |

The above ingredients are mixed to form a cosmetic cream.

INDUSTRIAL APPLICABILITY

The metal chelate compound of the present invention or a pharmacologically acceptable salt thereof has tyrosinase inhibiting activity, melanin production suppressing activity and elastase inhibiting activity, and therefore is useful as an agent for prophylaxis and treatment of blotches and freckles and suntan of the skin, a whitening agent, a skin-beautifying agent and an anti-wrinkle agent.

Furthermore, the metal chelate compound of the present invention is also useful for prophylaxis and treatment of a variety of disorders induced by oxidative stress, such as ischemic cardiovascular disease, cerebral ischemia, arteriosclerosis, diabetes mellitus and cataract.

Some of the embodiments of the present invention are described in detail above. However, as various modifications and changes can be made by those who skilled in the art to the specific embodiments without substantially departing from the novel disclosure and benefit of the present invention, all of such modifications and changes also fall within the spirit and scope of the present invention defined by the following claims.

The present application is based on Japanese patent application No. 2001-078571, filed in Japan, and all the contents thereof are included in the present application.

The invention claimed is:

1. A method of suppressing melanin production in human skin comprising, topically administering to a human an effective amount of an N-(6,8-dimercaptooctanoyl)amino acid metal chelate compound represented by the following formula (I),

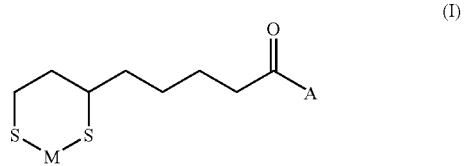

wherein M denotes a zinc, and A denotes an amino acid which is bound via the amino acid nitrogen; or a pharmacologically acceptable salt thereof, wherein the amino acid is selected from the group consisting of aminomethylcyclohexanoic acid, anthranilic acid, aminoethanesulfonic acid, glycine, alanine, valine, leucine, isoleucine, seine, threonine, tyrosine, cysteine, methionine, aspartic acid, asparagine, glutamic acid, glutamine, arginine, lysine, histidine, phenylalanine, tryptophan, β-alanine, γ-amino-n-butyric acid, carnitine, 5-aminolevulinic acid, 5-aminovaleric acid, and 6-aminohexanoic acid, wherein the human is in need of suppression of melanin production.

2. The method of claim 1, wherein the human is in need of whitening the skin.

3. The method of claim 1, wherein the human is in need of inhibiting elastase.

* * * * *